(12) United States Patent
Auriel et al.

(10) Patent No.: US 12,280,245 B2
(45) Date of Patent: Apr. 22, 2025

(54) DEVICE FOR MONITORING THE PRESSURE OR ALTERNATIVELY AN INJECTION FORCE OF A PLURALITY OF JETS GENERATED AT THE OUTLET OF A NEEDLELESS INJECTION DEVICE

(71) Applicant: CROSSJECT, Dijon (FR)

(72) Inventors: Christophe Auriel, Binges (FR); Ludovic Jaumary, Dijon (FR); Maxime Robin, Fontaines Saint Martin (FR); Brice Simonneau, Villeurbanne (FR)

(73) Assignee: CROSSJECT, Dijon (FR)

( * ) Notice: Subject to any disclaimer, the term of this patent is extended or adjusted under 35 U.S.C. 154(b) by 151 days.

(21) Appl. No.: 17/391,630

(22) Filed: Aug. 2, 2021

(65) Prior Publication Data

US 2021/0353864 A1  Nov. 18, 2021

Related U.S. Application Data

(63) Continuation of application No. PCT/FR2020/050158, filed on Jan. 31, 2020.

(30) Foreign Application Priority Data

Feb. 1, 2019  (FR) ...................................... 19/00997

(51) Int. Cl.
*A61M 5/30* (2006.01)

(52) U.S. Cl.
CPC ......... *A61M 5/30* (2013.01); *A61M 2205/332* (2013.01); *A61M 2205/3331* (2013.01)

(58) Field of Classification Search
CPC .................. A61M 5/30; A61M 5/3007; A61M 2005/3022; A61M 2205/332; A61M 2205/3331; A61M 5/2046; A61M 5/42; A61M 5/422; A61M 5/48; A61M 5/486; A61M 2205/70; A61M 2005/14288; A61M 5/16831; A61M 5/16854; A61M 5/16859

See application file for complete search history.

(56) References Cited

U.S. PATENT DOCUMENTS

2007/0055214 A1* 3/2007 Gilbert .................... A61M 5/30 604/500
2019/0336690 A1* 11/2019 Dyer ...................... A61M 5/30

FOREIGN PATENT DOCUMENTS

| CN | 103323174 | 2/2015 |
| FR | 2815544 | 4/2002 |
| JP | 2005021640 | 1/2005 |

(Continued)

OTHER PUBLICATIONS

International Search Report for International Application PCT/FR2020/050158, mailed Apr. 6, 2020.

*Primary Examiner* — Kami A Bosworth
*Assistant Examiner* — Avery Smale
(74) *Attorney, Agent, or Firm* — Burris Law, PLLC

(57) ABSTRACT

A monitoring device for monitoring a pressure or an injection force of a plurality of jets generated by channels at an outlet of a nozzle of a needleless injection device. The monitoring device includes a plurality of measuring elements. Each of the plurality of measuring elements are configured to measure the pressure or the injection force of a corresponding jet of the plurality of jets. Each of the plurality of measuring elements include a receiving face oriented to receive the corresponding jet.

11 Claims, 4 Drawing Sheets

(56) References Cited

FOREIGN PATENT DOCUMENTS

| | | | | |
|---|---|---|---|---|
| JP | 2005021640 A | * | 1/2005 | |
| WO | 2018069600 | | 4/2018 | |
| WO | WO-2018115249 A1 | * | 6/2018 | .............. A61M 5/19 |

* cited by examiner

DEVICE FOR MONITORING THE PRESSURE OR ALTERNATIVELY AN INJECTION FORCE OF A PLURALITY OF JETS GENERATED AT THE OUTLET OF A NEEDLELESS INJECTION DEVICE

CROSS-REFERENCE TO RELATED APPLICATIONS

This application is a continuation of International Application No. PCT/FR2020/050158, filed on Jan. 31, 2020, which claims priority to and the benefit of FR 19/00997 filed on Feb. 1, 2019. The disclosures of the above applications are incorporated herein by reference.

FIELD

The present disclosure relates to a device for monitoring the pressure or alternatively an injection force of a plurality of jets generated by channels at the outlet of a nozzle of a needleless injection device.

BACKGROUND

The statements in this section merely provide background information related to the present disclosure and may not constitute prior art.

Needleless, pre-filled and disposable injection devices are known, operating with an energy source such as for example a gas generator, and used for intradermal, subcutaneous and intramuscular injections of an active ingredient for therapeutic use in human or veterinary medicine.

The active ingredient consists of a liquid which may be viscous, a mixture of liquids, or a gel. The active ingredient may also be a solid dissolved in a suitable solvent for injection or consists of a pulverulent solid suspended at a certain concentration in a suitable liquid.

Such an injection device includes in a known manner, such as for example in the patent application FR 2 815 544 A, a body successively including a gas generator, an expansion chamber, a vessel containing the active ingredient and an injection system.

The vessel is inserted into a tubular housing of the body of the injection device, while being sealed by an upper or upstream plunger and a lower or downstream plunger. The lower free end of the vessel cooperates with the injection system including an injection nozzle including several injection channels extending axially along an injection axis. The diameter of the injection channels is compatible with the particle size of the active ingredient to inhibit it from being sealed.

In order to allow the injection of the active ingredient, the body is slidably mounted in a hollow cover enveloping the body, from bottom to top along a sliding axis, between a rest position and an injection position. The drive of the body is performed when the user presses the injection nozzle on his skin. The displacement of the body in the cover allows triggering of the gas generator, generating a pressurized gas which drives in displacement the plungers to inject the active ingredient through the skin of the patient, throughout the injection nozzle.

In this injection position, the active ingredient is ejected from the channels of the injection nozzle, in an injection direction, in jets having a predetermined injection pressure allowing the active ingredient to pass through the patient's skin at the desired depth to provide improved injection thereof. The injection pressure of these jets is therefore determinative of the depth of injection into the skin of the injected active ingredient.

Moreover, in order to allow successful injection, the jets at the outlet of the injection nozzle must be delivered according to this injection pressure for a predetermined injection time to provide for the injection of the desired amount of active ingredient.

These magnitudes of pressure, or alternatively of injection force, and injection time depend on the active ingredient to be injected.

There is therefore a need for a device for monitoring the pressure or alternatively the injection force of the jets generated by a needleless injection device, which allow for a faithful measurement of the pressure or alternatively of the injection force of these jets.

SUMMARY

This section provides a general summary of the disclosure and is not a comprehensive disclosure of its full scope or all of its features.

To this end, the present disclosure provides a device for monitoring the pressure or alternatively an injection force of a plurality of jets generated by channels at the outlet of a nozzle of a needleless injection device. The device for monitoring the pressure or alternatively a force according to the present disclosure is advantageous in that it includes, for each jet generated at the outlet of the nozzle, an element for measuring the pressure or alternatively an injection force of the corresponding jet. Each element for measuring the pressure or alternatively an injection force includes a face for receiving the corresponding jet oriented to receive this jet.

The independent measurement of the pressure or alternatively of the injection force of each of these jets advantageously makes it possible to identify subpar performance of an injection channel of a nozzle which does not deliver a jet according to a predetermined pressure or alternatively injection force. Identifying such subpar performance provides compliance of needleless injection devices during the control of a production batch for example.

According to one form of the present disclosure, at least the receiving face of an element for measuring the pressure or alternatively an injection force is inclined with respect to a plane orthogonal to the injection direction of the corresponding jet. The inclination of the receiving face of an element for measuring the pressure or alternatively an injection force makes it possible to limit the incidence of a neighboring jet on the receiving face of this element for measuring the pressure or alternatively an injection force.

According to a variation, the receiving face of each element for measuring the pressure or alternatively an injection force is inclined with respect to a plane orthogonal to the injection direction of the corresponding jet.

According to another variation, the inclination of each receiving face is oriented distinctly from one another.

According to another form of the present disclosure, the inclination of the receiving face of at least one element for measuring the pressure or alternatively an injection force is obtained by the tilting along its length of the element for measuring the pressure or alternatively an injection force corresponding to the plane orthogonal to the direction of injection.

According to a variation, the inclination of the receiving face of each element for measuring the pressure or alternatively an injection force is obtained by the tilting along its length of the corresponding element for measuring the pressure or alternatively an injection force relative to the injection direction.

According to another form of the present disclosure, at least one element for measuring the pressure or alternatively an injection force is formed by the assembly of a sensor of pressure or alternatively of an injection force and of an attached part including the face for receiving the corresponding jet.

According to a variation, the attached part advantageously includes a mechanical transmission element in contact with the pressure measuring element. The mechanical transmission element advantageously makes it possible to transmit the mechanical vibrations received by the attached part to the pressure measuring element.

According to another variation, the attached part is detachable from the pressure measuring element.

According to yet another variation, the receiving face is a beveled face of the attached part. In this configuration, for each element for measuring the pressure or alternatively an injection force, the sensor of pressure or alternatively of force extends in its length parallel to the injection direction of the corresponding jet. It should be understood that each sensor extends in a direction coaxial with the axis of an outlet channel through which the corresponding jet is projected.

According to an alternative form of the present disclosure, the device for monitoring the pressure or alternatively a force includes a support securely carrying each of the elements for measuring the pressure or alternatively an injection force.

According to a variation, the support may advantageously include lugs for indexing the elements for measuring the pressure or alternatively an injection force.

According to another variation, the indexing lugs advantageously allow the radial and axial indexing of the attached parts.

According to a variation, when an attached part is detachable from the pressure measuring element, it should be understood that it could be limited by the indexing lugs including indexing fingers provided for holding the attached part.

According to other variants, an attached part may be secured to the pressure measuring element by structural modifications such as: the addition of a liquid or viscous fastening element such as wax, glue, resin for example or by mechanical fastening such as crimping.

According to another variant of the present disclosure, the device for monitoring the pressure or alternatively a force includes a member for partitioning the jets with respect to one another.

According to a variation, the partitioning member makes it possible to inhibit the incidence of a neighboring jet on the receiving face of a corresponding measuring element.

According to another variation, the member for partitioning the jets may advantageously include separators delimiting the elements for measuring the pressure or alternatively an injection force from one another in order to inhibit the incidence of a neighboring jet on the receiving face of a corresponding element for measuring the pressure or alternatively an injection force.

According to another variant of the present disclosure, the device for monitoring the pressure or alternatively a force includes an element for indexing the channels of the nozzle with respect to the elements for measuring the pressure or alternatively an injection force.

According to a variation, the indexing element may advantageously include a base for receiving the nozzle and at least two indexing points intended to provide the positioning of the indexing element relative to the elements for measuring the pressure or alternatively an injection force.

According to another variant of the present disclosure, the device for monitoring the pressure or alternatively a force is composed of a force or pressure sensor and of an interface.

According to a variation, the interface allows the acquisition and the processing of the electrical signals transmitted by the elements for measuring the pressure or alternatively an injection force.

According to one form, the present disclosure also provides an assembly for monitoring the pressure or alternatively an injection force including a needleless injection device and a device for monitoring the pressure or alternatively an injection force as defined in the present disclosure.

According to one variation of this assembly, the needleless injection device includes a body successively including a gas generator, an expansion chamber, a vessel containing an active ingredient and an injection system, the injection system including the injection nozzle.

According to another variation, the body is slidably mounted in a hollow cover enveloping the body, along a sliding axis, between a rest position and an injection position.

According to yet another variation, the active ingredient contained in the vessel may advantageously be chosen from the group including the following active ingredients:
Methotrexate,
Adrenaline,
Sumatriptan,
Hydrocortisone,
Naloxone,
Midazolam,
Apomorphine,
Methylnaltrexone bromide,
Phytomenadione,
Chlorpromazine hydrochloride,
Zuclopenthixol acetate,
Danaparoid sodium,
Enoxaparin sodium,
Estradiol cypionate,
Medroxyprogesterone acetate,
Medroparin calcium,
Methylprednisolone acetate
Heparin calcium,
Terbutaline.

The present disclosure also provides a method for monitoring the pressure or alternatively an injection force of a plurality of jets generated by channels at the outlet of a nozzle of a needleless injection device. The method being carried out using a device for monitoring the pressure or alternatively a force as defined in the present disclosure.

The monitoring method is advantageous in that it includes: an indexing step in which the channels of the nozzle of the needleless injection device are placed opposite the elements for measuring the pressure or alternatively an injection force of the monitoring device; and a step of measuring the pressure or alternatively an injection force in which each of the jets is measured independently of one another.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

Figure 1:
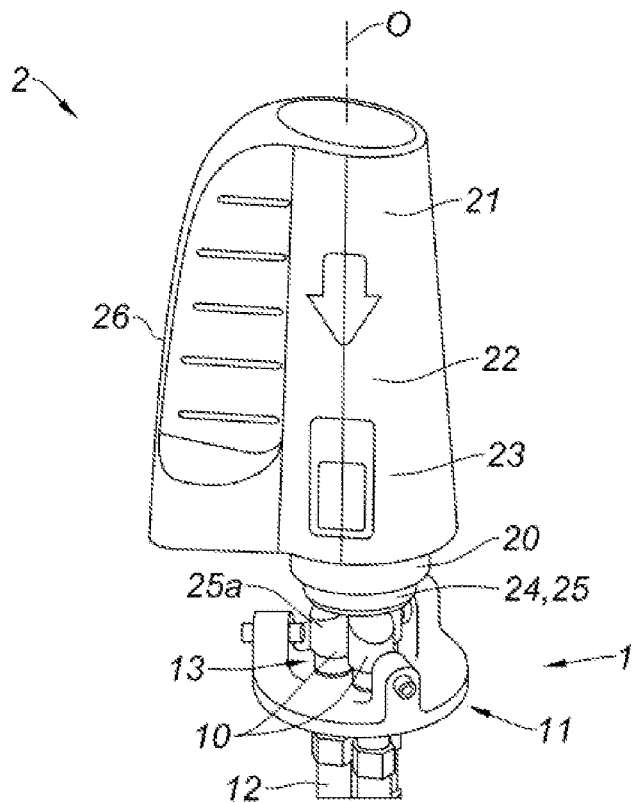
FIG. 1 is a perspective view of a monitoring device for monitoring the pressure or alternatively an injection force according to a first form of the present disclosure, illustrated with a needleless injection device.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

Figure 2:
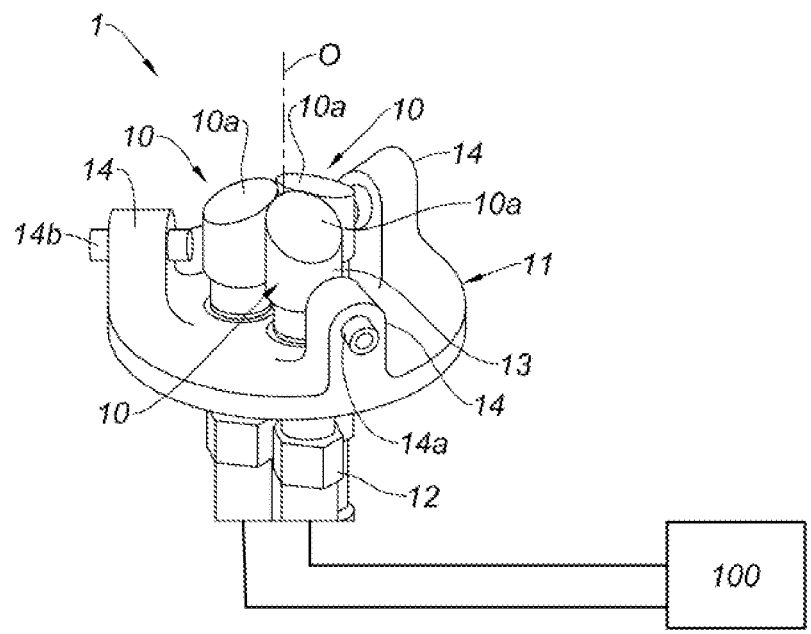
FIG. 2 is a perspective view of the monitoring device of FIG. 1, illustrated without the needleless injection device shown in FIG. 1.
Figure 3:
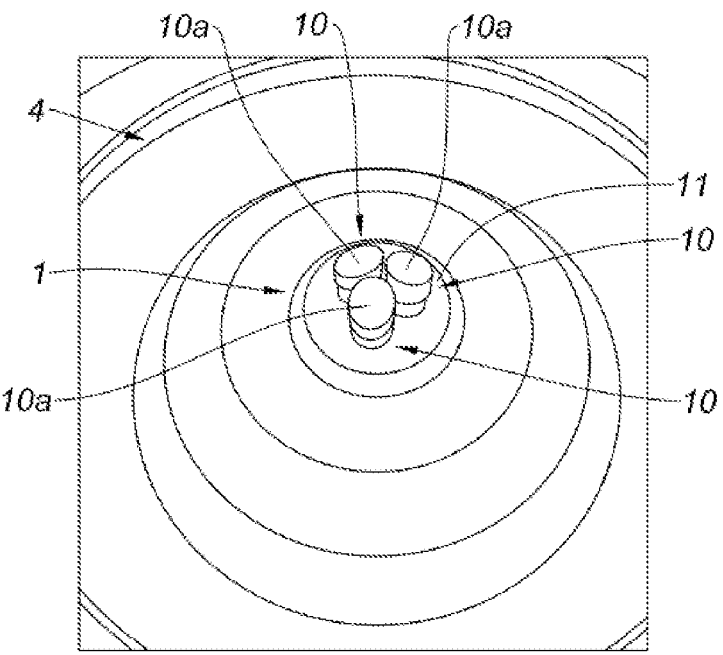
FIG. 3 is a perspective view of the monitoring device of FIG. 1, illustrated as being received in a base of an operational station in accordance with the teachings of the present disclosure.

In FIGS. 1 to 3, there is represented a device 1 for monitoring the pressure or alternatively an injection force according to a first form of the present disclosure. This device 1 for monitoring the pressure or alternatively an injection force is configured to measure the pressure or alternatively the injection force of each of the jets generated or ejected from an injection nozzle 25 of a needleless injection device 2 represented in FIG. 1. The needleless injection device 2 and the device 1 for monitoring the pressure or alternatively an injection force form an assembly for monitoring the pressure or alternatively an injection force dedicated to this measurement.

The represented needleless injection device 2, or needleless syringe, includes a body 20 successively including a gas generator 21, an expansion chamber 22, a vessel 23 actuated by upstream and downstream plungers and containing an active ingredient and an injection system 24 of the active ingredient.

The injection system 24 includes the injection nozzle 25 having a cylindrical shape around a main axis or injection direction O. The nozzle 25 is intended to cooperate with the body 20. The nozzle 25 includes at least one outlet channel 25a, the non-limiting example shown with three channels, parallel to the main injection axis O.

When the injection nozzle 25 is pressed, the body 20 slides in a hollow cover 26 enveloping it between a rest position and an injection position. The displacement of the body 20 in the cover 26 allows triggering of the gas generator 21, generating a pressurized gas which drives in displacement the plungers to eject the active ingredient from the injection nozzle 25.

The direction of propagation of these jets is parallel to the direction of injection O of the injection system 24.

In order to measure the pressure or the force of each of these jets, the injection nozzle 25 of the needleless injection device 2 is disposed opposite the device 1 for monitoring the pressure or alternatively an injection force.

The device 1 for monitoring the pressure or alternatively an injection force includes, for each jet generated by the nozzle 25 of the needleless injection device 2, an element 10 for measuring the pressure or alternatively an injection force dedicated to its measurement. It should then be understood that the measurement of each jet is carried out individually.

Each element 10 for measuring the pressure or alternatively an injection force is provided so as to be connected to a processing unit 100 acquiring the electrical signals transmitted by the elements 10 for measuring the pressure or alternatively an injection force. Each measuring element 10 is advantageously connected to the processing unit 100 by its free end.

In the example provided, these signals are processed independently of one another, though other configurations can be used.

The device 1 for monitoring the pressure or alternatively an injection force also includes a support 11 securely carrying each of the elements 10 for measuring the pressure or alternatively an injection force. The elements 10 for measuring the pressure or alternatively an injection force may advantageously be mounted on the support by screwing or else overmolded on the latter. For example, the body of the measuring element 10 may be tapped and a threaded opening of the support 11 may be configured to receive the measuring element 10.

The support 11 of the measuring elements 10 allows them to be positioned relative to one another such that they correspond to an arrangement allowing each of the measuring elements 10 to receive a corresponding jet.

By "corresponding jet" or "corresponding measuring element", it should be understood a jet or an element associated respectively with a measuring element or with a jet.

In order to allow the measurement of the pressure or alternatively of an injection force of each jet, each element 10 for measuring the pressure or alternatively an injection force of the corresponding jet includes a receiving face 10a onto which the corresponding jet is projected.

In order to limit the incidence of a neighboring jet on the receiving face 10a of a corresponding measuring element 10, the receiving face 10a of each measuring element 10 is inclined with respect to a plane orthogonal to the direction of injection of the corresponding jet. The inclination of each receiving face 10a is oriented distinctly from one another.

In this first form, each element 10 for measuring the pressure or an injection force is formed by the assembly of a sensor 12 of pressure or alternatively of injection force and of an attached part 13 including the face 10a for receiving the corresponding jet.

The attached part 13 is a complementary part to the sensor 12 of pressure or alternatively of force. The receiving face 10a of the measuring element 10 is a beveled face of the attached part 13.

In this first form of the present disclosure, each of the receiving faces 10a, herein the beveled faces of the measuring elements 10, is oriented radially outwards with respect to the main injection axis O. The incidence of a jet on a receiving face 10a is then projected radially outwards with respect to the main injection axis O.

The attached part 13 is advantageously configured to transmit to the sensor 12 of pressure or force the forces that it receives on its beveled face. For this purpose, without limitation, a mechanical transmission element may be provided so as to mechanically connect to one another, on one side, an inner face of the attached part 13 to the beveled face, and on the other side, a face of the sensor 12 of pressure or alternatively of force on which it is configured to apply a pressure or alternatively a force for measurement thereof. The mechanical transmission element may be formed by a blade, "Z"-like shaped, for example, the end faces of which connect the inner face of the attached part 13 to the face of the sensor 12 of pressure or alternatively of force, as defined before.

The sensor 12 of pressure or alternatively of force may advantageously be a piezoelectric sensor sensitive to the mechanical variations of the receiving face 10a when the latter receives the corresponding jet. When a jet is projected from a channel onto the receiving face 10a of the measuring element 10, the pressure or alternatively the force of this jet can then be measured.

The sensor 12 of pressure or alternatively of force can advantageously be a pencil-type sensor allowing placement thereof opposite a channel 25a of the injection nozzle 25 independently of the other elements 10 for measuring the pressure or an injection force. In other words, in the case of a plurality of channels 25a, the small-sized pencil-like sensors can be placed opposite the channels 25a of the injection nozzle 25 without being in contact with each other. The measurement of the pressure or alternatively of the injection force of each of the jets independently of one another is then improved.

The combination of a sensor 12 of pressure or alternatively of force with an attached part 13 including a beveled face advantageously makes it possible to extend the sensors 12 of pressure or alternatively of injection force along their length parallel to the injection direction of the corresponding jet. Such a configuration makes it possible to facilitate the assembly of the measuring elements 10 on the support 11. Moreover, the connection of the device 1 for monitoring the pressure or alternatively a force is thereby facilitated. Indeed, a free end of a sensor 12 can be inserted into a corresponding plug when the device 1 for monitoring the pressure or alternatively an injection force is housed in a base 4 (FIG. 3) of an operational station.

Indexing lugs 14 (FIG. 2) of the support 11 are provided for indexing the elements 10 for measuring the pressure or alternatively an injection force. More particularly, each of the indexing lugs 14 advantageously allows the radial and axial indexing of an attached part 13 which is associated with it. Each lug 14 includes a radial orifice 14a relative to the main injection axis O and receiving an indexing finger 14b intended to radially and axially index each of the attached parts 13 and advantageously provide their orientations with respect to each other.

It should then be understood that the indexing of the attached parts 13 by the indexing lugs 14 makes it possible to improve the measurement of the pressure or alternatively of a force of the jets by limiting the signal-to-noise ratio of the information transmitted by a corresponding measuring element 10.

Figure 4:
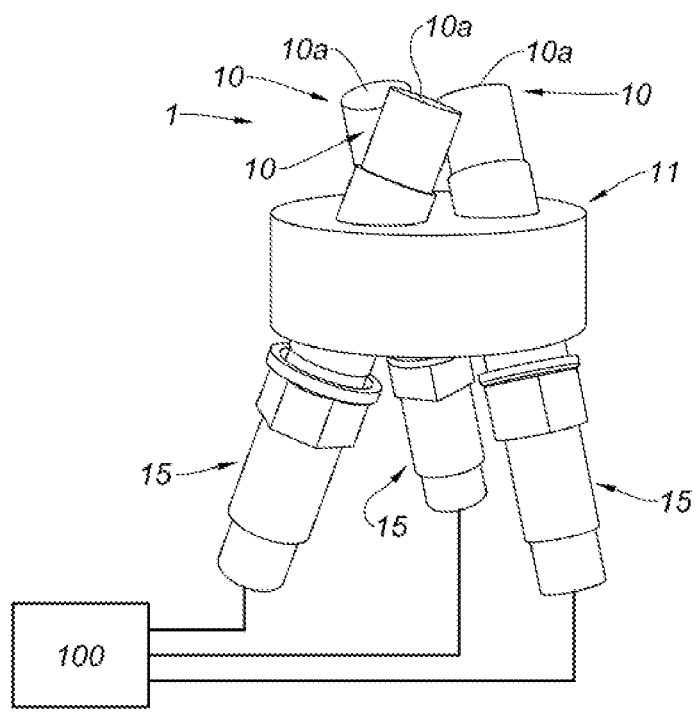
FIG. 4 is a perspective view of a monitoring device of a second form in accordance with the teachings of the present disclosure.

In FIG. 4, there is represented a second form of the present disclosure in which each element 10 for measuring the pressure or alternatively an injection force is formed integrally in one-piece by a pressure sensor 15.

In this second form, the inclination of the receiving face 10a of each element 10 for measuring the pressure or alternatively an injection force is obtained by the inclination along its length of the corresponding element 10 for measuring the pressure or alternately an injection force with respect to the injection direction O.

Similarly to the first form, the sensor 15 of pressure or alternatively of force may be formed by a piezoelectric sensor sensitive to the mechanical variations of the receiving face 10a when the latter receives the corresponding jet.

The measuring elements 10 may be mounted on the support 11 identically or similar to the first form.

The sensor 15 of pressure or alternatively of force may also be of the pencil type.

Figure 5:
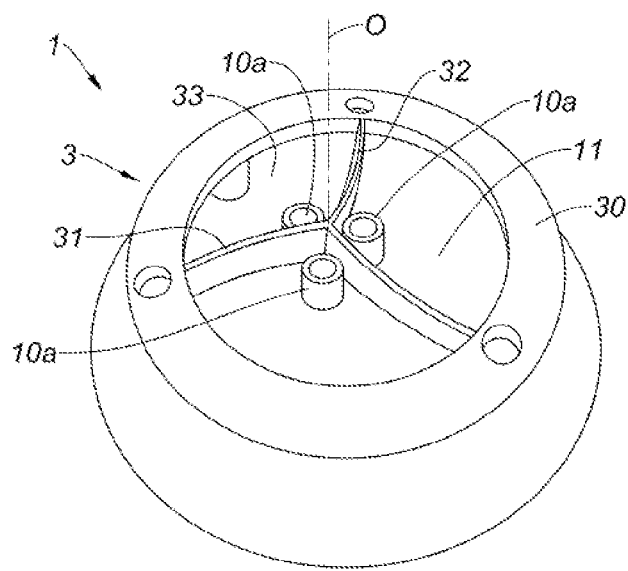
FIG. 5 is a perspective view of a monitoring device of a third form in accordance with the teachings of the present disclosure, the monitoring device including a member for partitioning the jets of the monitoring device.

In FIG. 5, there is represented a third form of the present disclosure in which the elements 10 for measuring the pressure or alternatively an injection force each has a receiving face 10a orthogonal to the injection direction O.

In this third form and in a manner that can be combined with any one of the first and second forms of the present disclosure, there is advantageously provided a member 3 for partitioning the jets with respect to one another. The member 3 for partitioning the jets is formed by a circular contour 30 from which separators 31, 32 interconnected by a central portion of the partitioning member 3 extend radially inwards with respect to the main injection axis O. The partitioning member 3 is advantageously mounted on feet 33 to be raised relative to the support 11 of the device 1 for monitoring the pressure or alternatively an injection force. When the partitioning member 3 is mounted on the support 11 or on the base 4 of a workstation, the separators 31, 32 delimit the measuring elements 10 from one another. More specifically, the separators 31, 32 are positioned in the direction of the main injection axis O to protrude from the receiving faces 10a of the measuring elements 10 while delimiting them. In this way, the partitioning member 3 makes it possible to inhibit the incidence of a neighboring jet on the receiving face 10a of a corresponding measuring element 10.

It should be understood that the member 3 for partitioning the jets makes it possible to improve the measurement of each of the jets.

Figure 6:
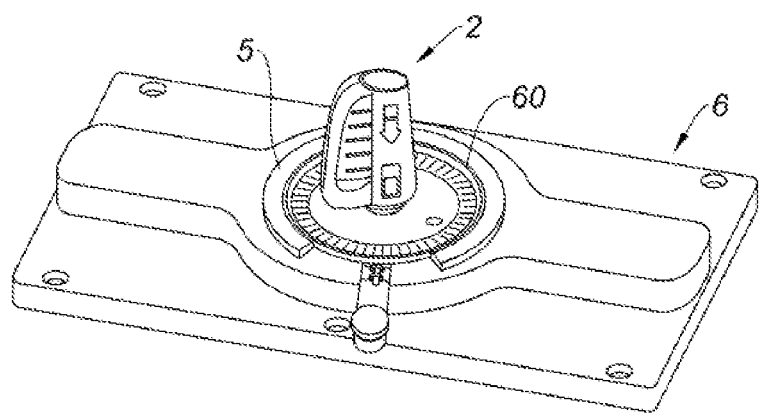
FIG. 6 is a perspective view of an indexing element in accordance with the teachings of the present disclosure, illustrated with the needleless injection device of FIG. 1.
Figure 7:
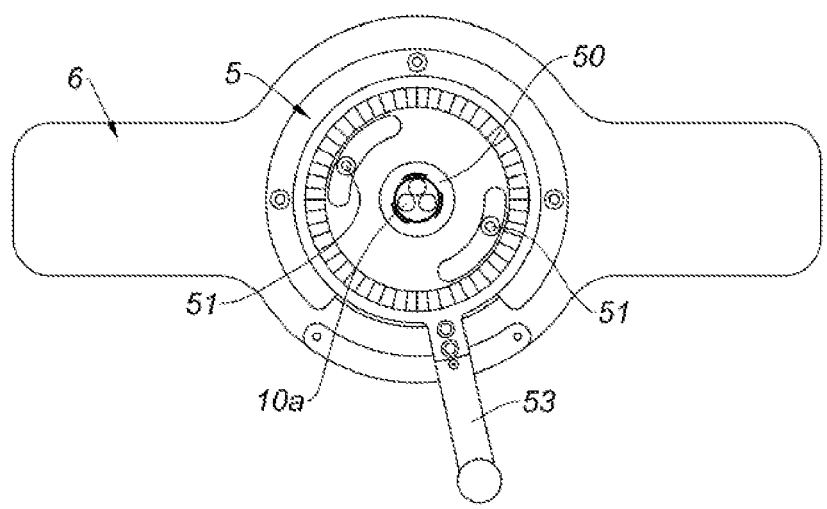
FIG. 7 illustrates a detailed view of the indexing element of FIG. 6.

In FIGS. 6 and 7, there is represented an element 5 for indexing the channels 25a of the injection nozzle 25 with respect to the elements 10 for measuring the pressure or an injection force.

As represented, the indexing element 5 is provided so as to be removably received in an opening 60 of a tray 6. At an operational station, this tray 6 is positioned so that the opening 60 provides access to the device 1 for monitoring the pressure or alternatively an injection force.

The indexing element 5 includes a base 50 for receiving the injection nozzle 25 and at least two indexing points 51 intended to provide the positioning of the indexing element 5 relative to the elements 10 for measuring the pressure or alternatively an injection force.

A lever 53 of the indexing element 5 makes it possible to manipulate it in rotation with respect to the main injection axis O, this being so to reach a final position where the indexing points 51 are placed in correspondence with a complementary portion of the tray 6.

In this final position, the channels 25a of the injection nozzle 25 are placed opposite the elements 10 for measuring the pressure or alternatively an injection force.

It should be understood that the indexing element 5 provides an accurate projection of each jet on the receiving face 10a of the corresponding measuring element 10.

The device 1 for monitoring the pressure or alternatively an injection force allows the implementation of a method for monitoring the pressure or alternatively an injection force of a plurality of jets generated by channels 25a at the outlet of a nozzle 25 of a needleless injection device 2.

The method is carried out using a device 1 for monitoring the pressure or alternatively an injection force according to any one of the forms of the present disclosure. This monitoring method includes at least: an indexing step in which the channels 25a of the nozzle 25 of the needleless injection device 2 are placed opposite the elements 10 for measuring the pressure or alternatively an injection force of the device 1 for monitoring the pressure or alternatively an injection force; and a step for measuring the pressure or alternatively an injection force in which each of the jets is measured independently of one another.

The measurement of these jets is advantageously carried out by the processing unit 100.

The present disclosure is not limited to the examples that have just been described and numerous modifications can be made to these examples without departing from the scope of the present disclosure. In particular, the different features, shapes, variants and forms of the present disclosure can be associated with each other according to various combinations to the extent that these are not incompatible or mutually exclusive. In particular, all previously-described variants and embodiments can be combined with one another.

Unless otherwise expressly indicated herein, all numerical values indicating mechanical/thermal properties, compositional percentages, dimensions and/or tolerances, or other characteristics are to be understood as modified by the word "about" or "approximately" in describing the scope of the present disclosure. This modification is desired for various reasons including industrial practice, material, manufacturing, and assembly tolerances, and testing capability.

As used herein, the phrase at least one of A, B, and C should be construed to mean a logical (A OR B OR C), using a non-exclusive logical OR, and should not be construed to mean "at least one of A, at least one of B, and at least one of C."

In this application, the term "controller" and/or "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components (e.g., op amp circuit integrator as part of the heat flux data module) that provide the described functionality; or a combination of some or all of the above, such as in a system-on-chip.

The term memory is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general-purpose computer to execute one or more particular functions embodied in computer programs. The functional blocks, flowchart components, and other elements described above serve as software specifications, which can be translated into the computer programs by the routine work of a skilled technician or programmer.

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A monitoring device for monitoring a pressure of or an injection force of a plurality of jets generated by channels at an outlet of a nozzle of a needleless injection device, the monitoring device comprising:
a plurality of measuring elements, each of the plurality of measuring elements configured to measure the pressure of or the injection force of a corresponding jet of the plurality of jets, each of the plurality of measuring elements comprising a receiving face oriented to receive the corresponding jet, wherein the receiving face of at least one of the plurality of measuring elements is inclined with respect to a plane orthogonal to a direction of propagation of the corresponding jet.

2. The monitoring device according to claim 1, wherein an inclination of the receiving face of the at least one of the plurality of measuring elements is obtained by tilting along a length of the at least one of the plurality of measuring elements with respect to the plane orthogonal to the direction of propagation.

3. The monitoring device according to claim 1, wherein at least one of the plurality of measuring elements are formed by an assembly of a pressure sensor or an injection force sensor and a part comprising the receiving face.

4. The monitoring device according to claim 1, further comprising a support securely carrying each of the plurality of measuring elements.

5. The monitoring device according to claim 4, wherein the support comprises lugs for indexing the plurality of measuring elements.

6. The monitoring device according to claim 1, further comprising a partitioning member for partitioning the plurality of jets from one another.

7. The monitoring device according to claim 6, wherein the partitioning member comprises separators for delimiting the plurality of measuring elements from one another in order to inhibit an incidence of a neighboring jet of the plurality of jets on the receiving face of a corresponding measuring element of the plurality of measuring elements.

8. The monitoring device according to claim 1, further comprising an indexing element for indexing the channels of the nozzle relative to the plurality of measuring elements.

9. The monitoring device according to claim 8, wherein the indexing element comprises a receiving base of the nozzle and at least two indexing points configured to provide a positioning of the indexing element relative to the plurality of measuring elements.

10. An assembly comprising a needleless injection device and the monitoring device according to claim 1.

11. A monitoring method for monitoring a pressure of or an injection force of a plurality of jets generated by channels at an outlet of a nozzle of a needleless injection device, the monitoring method being carried out using the monitoring device according to claim 1, wherein the monitoring method comprises:
- an indexing step wherein the channels of the nozzle of the needleless injection device are placed opposite the plurality of measuring elements of the monitoring device; and
- a step for measuring the pressure of or the injection force of the plurality of jets wherein the pressure of or the injection force of each of the plurality of jets is measured independently from one another.

* * * * *